United States Patent [19]

Hoefnagel et al.

[11] Patent Number: 5,679,865
[45] Date of Patent: Oct. 21, 1997

[54] PROCESS FOR THE PREPARATION OF POLYHYDROXYBENZOPHENONES

[75] Inventors: Anthonius Johannes Hoefnagel; Herman van Bekkum, both of Delft, Netherlands

[73] Assignee: Technische Universiteit Delft, Netherlands

[21] Appl. No.: 666,999

[22] Filed: Jun. 21, 1996

Related U.S. Application Data

[63] Continuation of Ser. No. 331,595, Dec. 20, 1994, abandoned.

[30] Foreign Application Priority Data

May 6, 1992 [EP] European Pat. Off. ............. 92201285

[51] Int. Cl.$^6$ .................................................... C07C 45/45
[52] U.S. Cl. ............................................ 568/319; 568/323
[58] Field of Search .................................. 568/319, 323

[56] References Cited

U.S. PATENT DOCUMENTS

| | | | |
|---|---|---|---|
| 4,304,941 | 12/1981 | Lee et al. | 568/319 |
| 4,453,010 | 6/1984 | Staniland | 568/319 |
| 4,668,826 | 5/1987 | Gupta | 568/319 |
| 4,960,943 | 10/1990 | Botta et al. | 568/322 |
| 5,227,529 | 7/1993 | Neuber et al. | 568/322 |

FOREIGN PATENT DOCUMENTS

| | | | |
|---|---|---|---|
| 279322 | 2/1988 | European Pat. Off. | 568/322 |
| 473023 | 3/1992 | European Pat. Off. | 568/319 |
| 2667063 | 3/1992 | France | 568/319 |

OTHER PUBLICATIONS

A.J. Hoefnagel et al., "Direct Fries reaction of resorcinol with benzoic acids catalyzed by zeolite H–beta", Applied Catalysis A: General, 97 (1993), 87–102.

*Primary Examiner*—James H. Reamer
*Attorney, Agent, or Firm*—Michaelson & Wallace; Peter L. Michaelson; Edward M. Fink

[57] ABSTRACT

The invention relates to a process for the preparation of polyhydroxybenzophenones by treating benzoic acid or a derivative thereof with a polyhydroxybenzene or a derivative thereof in the presence of a large pore zeolite as a catalyst.

4 Claims, No Drawings

PROCESS FOR THE PREPARATION OF POLYHYDROXYBENZOPHENONES

CROSS REFERENCE TO RELATED APPLICATION

This application is a continuation of patent application Ser. No. 08/331,595 entitled "Process for the Preparation of Polyhydroxybenzophenones" filed on Dec. 20, 1994 now abandoned.

The invention relates to a process for the preparation of polyhydroxybenzophenones. More in particular, the invention relates to a process for the preparation of polyhydroxybenzophenones by treating benzoic acid or a derivative thereof with a polyhydroxybenzene in the presence of a large pore zeolite as a catalyst.

Polyhydroxybenzophenones are known as useful intermediates for many reactions. For example, 2,4-dihydroxybenzophenone is an intermediate in the preparation of 4-O-octyl-2-hydroxybenzophenone, useful as UV absorbent. Many methods of preparing these polyhydroxybenzenes are known.

According to British patent specification 947,686, polystyrene plastics are made stable to ultraviolet light by addition of certain benzophenone derivatives. According to this patent specification, benzophenone derivatives were produced by reacting o-toluic acid and resorcinol (1,3-benzenediol). However, HCl is used in this process, which leads to an inferior product.

Fries rearrangements [K. Fries and G. Finck, Chem. Ber., 41, 4271 (1908)] in which catalysts such as $AlCl_3$, $ZnCl_2$, $HgCl_2$, $SnCl_4$ and $FeCl_3$ are used, can also be useful in the preparation of polyhydroxybenzophenones. The preparation of 2,4-dihydroxybenzophenone can be accomplished with a good yield by the metal chloride catalyzed reaction of resorcinol with benzotrichloride, leading to the production of hydrochloric acid (Chem.Abstr.87, 210102 (1977)).

Fries rearrangements in which catalysts such as polymeric perfluorinated sulfonic acid resin (Nafion-H) and ion-exchange resin (Amberlyst-15) are used, have also been reported. The Fries arrangement of aryl benzoates in the presence of ion-exchange resin catalysts is known from, e.g., Chemical Abstracts 104, 109139u, where reacting aryl benzoates in the presence of Nafion-XR or Amberlite 200C, as a result of a Fries rearrangement, leads to the preparation of the corresponding benzophenones.

Chemical Abstracts 111, 7061q, discloses the preparation of polyhydroxybenzophenones by benzoylation of polyhydroxybenzenes, in the presence of a sulfonic acid. According to this process, Amberlyst-15 was used as a catalyst in the reaction of pyrogallol (1,2,3-benzenetriol) and pohydroxybenzoic acid in the presence of toluene under azeotropical removal of water to give 2,3,4,4'-tetrahydroxybenzophenone.

A direct Fries reaction of resorcinol and benzoic acid is given in the following Figure:

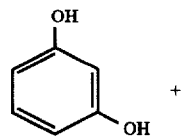

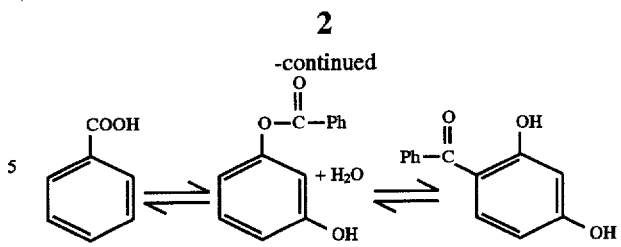

Water is the only by-product of the reaction, which can easily be removed.

The known processes to prepare benzophenone derivatives catalyzed by ion-exchange resins show some severe drawbacks, for instance, in the reaction of resorcinol with benzoic acid, where resorcinol dibenzoate is produced as a by-product and the resin is polluted with another, coloured, by-product. The formation of this coloured by-product, which is assumed to be 3,6-dioxy-9-phenyl-xanthydrol, decreases the yield of the desired compound and therefore lowers the efficiency of the process.

Amberlyst-15 is known to enhance the production of this coloured by-product, which renders the catalyst unusable after a period of time. Regeneration of such a catalyst is not possible as it will decompose at temperatures exceeding 200°–250° C. Another drawback of the use of Amberlyst-15 is the fact that resorcinol is bound to the catalyst during the reaction, as a result of a sulfonation of this compound by the $SO_3H$ groups of the catalyst. This also diminishes the efficiency of a regeneration of the catalyst.

The object of the present invention is to provide a process for the preparation of polyhydroxybenzophenones which does not have the drawbacks of the known processes.

The invention provides a method which allows polyhydroxybenzophenones to be produced with a good yield, with a minimized production of unwanted by-products.

Surprisingly, it has been found that using a large pore zeolite in the reaction of benzoic acid or a derivative thereof with a polyhydroxybenzene enables the reaction to be carried out in a one-pot operation, with a very good product yield, and without any, or with a strongly diminished, formation of unwanted by-products such as dibenzoates or any other by-products that decrease the efficiency of the catalyst.

The invention is therefore directed to a process for the preparation of polyhydroxybenzophenones by treating benzoic acid or a derivative thereof with a polyhydroxybenzene or a derivative thereof in the presence of a large pore zeolite as catalyst. Preferably, the large pore zeolite catalyst is zeolite beta, and most preferred is zeolite H-beta, i.e., zeolite beta in the proton acid form.

In the method according to the invention the esterification reaction and Fries rearrangement reaction are catalyzed with one and the same catalyst in a one-pot operation, which simplifies the procedure and also diminishes the waste problem of the aforementioned known reactions with metal chlorides.

As all mother liquors, filtrates and washings that are used in the method according to the present invention can be recycled, and substantially no by-products are produced, the process is environmentally friendly whereas the known processes are not.

The use of a large pore zeolite, and more in particular of zeolite H-beta, does not lead to substantial production of the coloured by-product or dibenzoate esters. Additionally, the reaction mixture containing the end product can easily be separated from the catalyst by decantation, after which the product is isolated by extraction, for example with methanol.

A large pore zeolite is defined herein as a zeolite having pores with diameters equal to or larger than 0.6 nm, and preferably between 0.7 and 0.8 nm (Holderich, W. F. and van Bekkum, H., "Introduction to Zeolite Science and Practice", eds. van Bekkum, H., Flanigen, E. M. and Jansen, J. C., Elsevier, Amsterdam (1990), page 632).

The diameters of zeolites are obtained using X-ray techniques and absorption measurements. Newsam, J. M. et.al., Proc.R.Soc., London, A 240 (1988), page 375, describe the pore structure of zeolite beta in more detail.

The reaction can be carried out in conventional equipment suitable for this kind of chemical reactions.

The reaction suitably takes place by introducing the reactants, solvent, if any, and catalyst in the reactor with stirring under conditions of temperature and pressure suitable for the reaction to run. The reaction can be carried out continuously, discontinuously or semi-continuously.

Compounds which can be reacted using the method according to the present invention are polyhydroxybenzenes or derivatives thereof and benzoic acid or derivatives thereof.

Polyhydroxybenzenes can be substituted with one or more alkyl groups and/or halogen atoms. Resorcinol and derivatives thereof are preferred.

Benzoic acid can be substituted with one or more alkyl groups, like methyl or ethyl, and/or hydroxy atoms. o-Toluic acid and benzoic acid are preferred.

The reaction can be carried out in the presence or absence of a solvent. Preferably a solvent is used.

The solvent in which the reaction can be performed is preferably a high boiling, inert solvent, preferred boiling point at least 110° C., in which the starting materials, as well as the products, are soluble. The solvent does preferably not form a stable mixture with water.

Suitable solvents are, for example, n-butylbenzene (bp 182° C.), p-chlorotoluene (bp 162° C.), mesitylene (bp 165° C.), n-decane (bp 174° C.), and chlorobenzene (bp 130° C.). Preferred solvents are n-butylbenzene and p-chlorotoluene.

If a solvent is present, the polyhydroxybenzene and derivatives thereof and benzoic acid and derivatives thereof are each present in an amount of at least 1% by weight of the solvent, and the solubility in the solvent determines the maximum amount present.

In any case it is preferred that the reacting compounds are present in equimolar or substantially equimolar amounts, i.e., the molar ratio of benzoic acid to polyhydroxybenzene ranges from 0.5:1 to 2:1, preferably from 0.9:1 to 1.25:1.

If desired, the reaction can be performed under a nitrogen atmosphere.

The reaction temperature is preferably reflux temperature, and reaction times will be in the range of 10 minutes to 10 hours, more particularly in the range of 1 to 4 hours.

The pressure to be used is not critical. Atmospheric, sub-atmospheric and supra-atmospheric pressures may be used. In view of the ease thereof, atmospheric pressure is preferred.

A major amount of the reaction product can be obtained by simple decantation of the final reaction mixture and catalyst, and another part of the reaction product can be obtained by extraction of the catalyst with a suitable solvent, for example an alcohol like methanol, followed by a washing step with a suitable non-solvent like n-pentane and a drying step.

The filtrate (the solvent, if present) and catalyst can be reused after the reaction. The catalyst can be regenerated at elevated temperatures in the range of 250° to 450° C. The regeneration temperature is dependent on the type of catalyst. Zeolite H-beta can be regenerated at temperatures up to 400° C.

In a preferred embodiment of the invention, resorcinol is reacted with benzoic acid in n-butylbenzene in the presence of zeolite H-beta, resulting in 2,4-dihydroxybenzophenone.

In another preferred embodiment of the invention, 2-methylresorcinol is reacted with 2-methylbenzoic acid in p-chlorotoluene in the presence of zeolite H-beta, resulting in 2,4-dihydroxy-2',3-dimethylbenzophenone.

The invention will now be elucidated in and by the following examples, which are not intended to restrict the invention.

EXAMPLE 1

Calcination of the zeolite catalyst

Zeolite beta (molar ratio Si/Al=14, Exxon Chemical, Rotterdam) was calcined at 550° C. for two days. After calcination, the zeolite was refluxed three times for one hour, with an 1M ammonium nitrate solution, filtered off, washed with water, dried at 100° C. for one hour and subsequently calcined at 550° C. for two days.

Before use, the catalyst was heated to 400° C.

All other chemicals were commercial analytical grade products and were used without further purification.

Preparation of 2,4-diOH-2',3-di-Me-benzophenone 1.55 g (12.5 mmol) 2-Me-resorcinol, 1.70 g (12.5 mmol) 2-Me-benzoic acid, 1.25 g zeolite H-beta (after activation at 400° C.) and 50 ml n-decane were mixed. The mixture was stirred at reflux temperature (oil bath 190° C.) with removal of condensed water (from a Dean-Stark condenser).

The course of the reaction was followed by GC-analysis (VARIAN, model 3700 GC, using a 50M capillary column (sil 5 CP) at a temperature of 225° C.).

After 3 h of refluxing, the yield of 2,4-diOH-2',3-di-Me-bensophenone was 90.7%.

After warm decantation of the clear light yellow solution, practically pure 2,4-diOH-2',3-di-Me-benzophenone precipitated. Filtration gave 1.6 g of a light yellow product.

A second portion (0.75 g) was obtained by extraction of the catalyst and reaction flask with methanol (40° C.). After washing with n-pentane, the yield was 2.20 g product (98% purity), i.e., 73% of the theoretical maximum.

M.p 187°–188.5° C.

$^1$HNMR analysis was in agreement with the proposed structure. The filtrate (n-decane) and the catalyst can be reused directly or after re-activation by heating for 2 hours at 400° C.

EXAMPLE 2

Preparation of 2,4-diOH-2',3-di-Me-benzophenone

According to the method of Example 1, 2-Me-resorcinol and 2-Me-benzoic acid were reacted in the presence of zeolite H-beta (after activation at 400° C.). 50 ml p-chlorotoluene was used as a solvent.

After 2 h of refluxing, the yield of 2,4-diOH-2',3-di-Me-benzophenone was 92%.

After warm filtration—to remove the catalyst—the filtrate, after cooling, filtration, washing with n-pentane and drying, gave 2.25 g (i.e. 74% of the theoretical value)

2,4-diOH-2',3-di-Me-benzophenone, with a purity of 97% and a m.p. of 187°–188.5° C.

EXAMPLE 3

Preparation of 2,4-diOH-2'-Me-benzophenone

According to the method of Example 1, 2.20 g (20 mmol) of resorcinol was reacted with 2.72 g (20 mmol) 2-Me-benzoic acid in 50 ml of mesitylene, in the presence of 2.00 g of zeolite H-beta (after activation at 400° C.) as a catalyst.

After 3 h of refluxing with removal of condensed water from the condenser, the yield of 2,4-diOH-2'-Me-benzophenone was 90%, according to GC-analysis.

Further processing according to the method of Example 1 yielded 3.48 g (i.e. 76% of the theoretical value) of a practically pure product (98% purity) with a melting point of 121°–123° C.

The catalyst can be regenerated by heating at 400° C. for 1 h after removal of the remainder of the reaction products and can be reused together with the filtrates.

EXAMPLE 4

Preparation of 2,4-diOH-2'-Me-benzophenone

The method according to Example 3 was repeated with 50 ml of p-chlorotoluene as solvent.

Further processing according to the method of Example 1 yielded 3.47 g (i.e. 76% of the theoretical value) of practically pure 2,4-diOH-2'-Me-benzophenone (98% purity) with a melting point of 121°–123° C.

EXAMPLE 5

Preparation of 2,4-diOH-benzophenone and recycling of the catalyst and filtrate

A mixture of 1.10 g (10 mmol) of resorcinol, 1.22 g (10 mmol) of benzoic acid, 1.00 g zeolite H-beta (activated at 400° C.) and 40 ml of n-butylbenzene was refluxed with stirring for 3 hours in a nitrogen atmosphere, resulting in an equilibrium mixture containing 11% of benzoic acid, 11% of resorcinol, 23% of resorcinol monobenzoate and 55% of 2,4-di-OH-benzophenone.

Isolation of 0.85 g (40% of the theoretical value) of the light-yellow coloured product 2,4-diOH-benzophenone with a m.p. of 142°–143.5° C. was accomplished by warm filtration, followed by filtration of the cooled filtrate (20° C.) and drying of the precipitate after washing with pentane and water.

Recycling procedure

Recycling of the filtrate and the residues, obtained after evaporation of the extracts of the precipitate (extracted with pentane and water) and of the catalyst (extracted with methanol), in combination with the regenerated catalyst and with replenishment of 4 mmol of benzoic acid and of resorcinol, resulted in an equilibrium mixture containing 5% of benzoic acid, 5% of resorcinol, 24% of resorcinol monobenzoate and 66% of 2,4-dihydroxybenzophenone.

The reduced formation of water thus resulted in a more complete esterification reaction.

Isolation and purification according to the method of Example 1, produced 0.75 g (35%) of practically pure (98%) 2,4-di-OH-benzophenone with a m.p. of 144°–145° C.

A conversion of the additionally added 4 mmol of benzoic acid and of resorcinol into 88% of practically pure 2,4-dihydroxybenzophenone has thus occurred.

Comparative Examples

According to the method of Example 1, 10 mmol resorcinol was reacted with 10 mmol benzoic acid in 25 ml chlorobenzene, in the presence of various catalysts. The catalysts were present in an amount of 1 mmol or 1.0 g (zeolite or ion-exchange resin).

The yield of 2,4-diOH-benzophenone was determined and the production of by-products was measured.

The results are summarized in the following Table.

TABLE

Reaction mixtures obtained after refluxing of a solution of resorcinol and benzoic acid in chlorobenzene, using various catalysts.

| Catalyst | time h | resorcinol monobenzoate % | 2,4-diOH-benzo phenone % | resorcinol dibenzoate |
|---|---|---|---|---|
| $H_3PO_4$ | 24 | 55 | 9 | — ** |
| $CH_3SO_3H$ | 23 | 32 | 17 | — |
| Amberlyst 15 * | 6 | 16 | 67 | 4 |
|  | 23 | 15 | 62 | 10 |
| Nafion 117 * | 6 | 24 | 46 | 2 |
|  | 24 | 23 | 45 | 3 |
| Zeolite H-beta | 4 | 16 | 10 | — |
|  | 24 | 17 | 20 | trace |

\* Ion-exchange resins were intensively coloured after reaction.
\*\* not detectable.

The results of the Table clearly show that the use of ion-exchangers such as Amberlyst-15 or Nafion 117 as a catalyst, leads to the production of resorcinol dibenzoate as a by-product.

Further, the ion-exchangers were polluted with a coloured by-product, which is assumed to be 3,6-dioxy-9-phenyl-xanthydrol. This by-product decreases the yield of the desired compound and therefore diminishes the efficiency of the process. Also, resorcinol is sulfonated and bound to the ion-exchangers, which also diminishes the efficiency of the reaction.

In using zeolite beta as a catalyst, hardly any resorcinol dibenzoate is produced and the catalyst is not intensively coloured. Zeolite beta, unlike ion-exchangers, is easily regenerated at high temperatures, for example at 250° to 400° C., to remove any organic material and water.

We claim:

1. Process for the preparation of polyhydroxy-benzophenones which comprises reacting (a) benzoic acid and derivatives thereof having one or more alkyl groups, one or more hydroxy groups and mixtures thereof, and (b) polyhydroxybenzene and derivatives thereof having one or more alkyl groups, one or more halogen atoms and mixtures thereof in the presence of a zeolite catalyst having pore diameters of at least 0.6 nm.

2. Process in accordance with claim 1 wherein reaction is effected in the presence of an inert solvent having a boiling point of at least 110° C.

3. Process in accordance with claim 1 wherein the molar ratio of benzoic acid to polyhydroxybenzene is within the range of 0.5:1 to 2:1.

4. Process in accordance with claim 3 wherein the molar ratio is within the range of 0.9:1 to 1.25:1.

* * * * *